United States Patent [19]
Coy et al.

[11] Patent Number: 4,897,445
[45] Date of Patent: Jan. 30, 1990

[54] METHOD FOR SYNTHESIZING A PEPTIDE CONTAINING A NON-PEPTIDE BOND

[75] Inventors: David H. Coy; Simon J. Hocart, both of New Orleans, La.

[73] Assignee: The Administrators of the Tulane Educational Fund, New Orleans, La.

[21] Appl. No.: 164,068

[22] Filed: Mar. 4, 1988

Related U.S. Application Data

[62] Division of Ser. No. 879,348, Jun. 27, 1986, Pat. No. 4,803,261.

[51] Int. Cl.$^4$ ..................... C08F 283/00; A61K 37/02
[52] U.S. Cl. ................................... 525/54.11; 530/323
[58] Field of Search ....................... 530/334, 332, 323; 525/54.11

[56] References Cited

U.S. PATENT DOCUMENTS 4,569,967  2/1986  Kornreich ..................... 525/54.11

FOREIGN PATENT DOCUMENTS 2117777  10/1983  United Kingdom .

OTHER PUBLICATIONS

Szelke et al. (1982) Nature 299:555.
Tourwe et al. "The synthesis of Peptide Analogues with a Modified Peptide Bond".
Natarajan et al. (1981) Proc. 7th Am. Peptide Symp.; ed. by D. N. Rich and E. Gross, p. 429.
Hudson et al. (1979) Int. J. Peptide Protein Research, 14: 177.

Primary Examiner—John Kight
Assistant Examiner—Nathan M. Nutter

[57] ABSTRACT

This invention features a method for the solid phase synthesis of non-peptide bonds ($CH_2$—NH) in polypeptide chains. These polypeptides are synthesized by standard procedures and the non-peptide bond synthesized by reacting an amino aldehyde and an amino acid in the presence of $NaCNBH_3$.

This invention also features somatostatin analogs with non-peptide bonds.

This invention further features a solid phase method of chemically modifying a peptide. The method involves synthesizing α-N-R and side group N-R analogs of peptides, where R is a an alkyl or aryl group, by reacting a carbonyl-containing compound and an amino acid in the presence of $NaCNBH_3$.

7 Claims, 3 Drawing Sheets

Ac-D-Nal-D-Phe-D-Phe-Ser(Bzl)-Tyr(Bzl)-D-Lys(FMOC)-Phe-Lys(FMOC)-Pro-D-Ala-benzhydrylamine resin ↓ 50% Piperidine/DMF, 12h Ac-D-Nal-D-Phe-D-Phe-Ser(Bzl)-Tyr(Bzl)-D-Lys-Phe-Lys-Pro Ala-benzhydrylamine resin ↓ acetone/NaCNBH$_3$/DMF Ac-D-Nal-D-Phe-D-Phe-Ser(Bzl)-Tyr(Bzl)-D-Lys(iPr)-Phe-Lys(iPr)-Pro-Ala-benzhydrylamine resin ↓ HF/anisole Ac-D-Nal-D-Phe-D-Phe-Ser-Tyr-D-Lys(iPr)-Phe-Lys(iPr)-Pro-Ala-NH$_2$ Abbreviations:   FMOC:   fluorenylmethyloxycarbonyl
                    iPr:    epsilon isopropyl
                    BZL:    benzyl

FIG.3

METHOD FOR SYNTHESIZING A PEPTIDE CONTAINING A NON-PEPTIDE BOND

This application is a divisional application of U.S. Ser. No. 06/879,348 filed June 27, 1986 and now U.S. Pat. No. 4,803,261.

BACKGROUND OF THE INVENTION

This invention relates to the synthesis of polypeptide chains containing non-peptide bonds and to the chemical modifications of polypeptide chains.

Normally amino acids within a polypeptide chain are bonded together by a covalent peptide bond of the formula —CO—NH—. A variety of enzymes (proteases) can act on this bond and hydrolyze it to break the polypeptide chain into two or more fragments.

Szelke et al. (1982, Nature 299:555) describe the formation of analogs of angiotensinogen by the chemical modification of peptide bonds within the polypeptide angiotensinogen. The modified bonds have the formula —CH$_2$—NH—, and some of the analogs containing those bonds were found to have increased potency compared to native angiotensinogen. It was hypothesized that this increased potency was due to the inability of proteases to cleave the non-peptide bond. Some of the analogs were synthesized from dipeptides formed in solution by reduction alkylation of an amino acid with an amino aldehyde, using NaCNBH$_3$. The dipeptide was purified by gel filtration and ion-exchange chromatography before completion of the synthesis of the analog.

SUMMARY OF THE INVENTION

In a first aspect the invention features a method of solid-phase synthesis of a polypeptide having a non-peptide bond. The method involves providing an amino aldehyde of the formula:

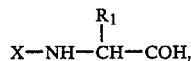
  (1)

where X includes a protecting group and R$_1$ is a side group of an amino acid; providing a complex of the formula:

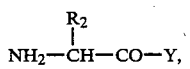
  (2)

where Y includes a solid phase and R$_2$ is a side group of an amino acid; and reacting the amino aldehyde with the complex in the presence of sodium cyanoborohydride to form:

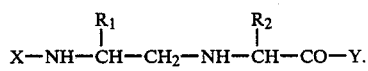
  (3)

Additional amino acids can then be added to the chain, if desired, and the peptide is then cleaved from the solid-phase to release the polypeptide, which is then purified.

In a second aspect the invention features a method of solid-phase chemical modification of a peptide. The method involves providing a carbonyl - containing compound of the formula:

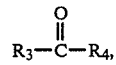
  (4)

where R$_3$ and R$_4$, independently, include hydrogen; branched or straight chain lower (C$_1$–C$_6$) alkyl group, e.g., methyl; or aryl group, e.g., phenyl, p-chloro-phenyl, or naphthyl; providing a complex of the formula:

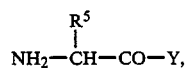
  (5)

where Y includes a solid phase and R$_5$ is a side group of an amino acid; and reacting the carbonyl-containing compound with the complex in the presence of sodium cyanoborohydride to form:

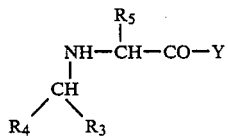
  (6)

Additional amino acids can then be added to the chain, if desired and the peptide is then cleaved from the solid-phase to release the peptide, which is then purified. In preferred embodiments, the carbonyl-containing compound is formaldehyde (R$_3$=R$_4$=H).

In a third aspect the invention features a method of solid-phase chemical modification of a peptide containing amino acid subunits which contain NH$_2$— containing side groups. The method involves providing a carbonyl-containing compound of the formula:

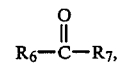
  (7)

where R$_6$ and R$_7$, independently, include hydrogen; branched or straight chain lower (C$_1$–C$_6$) alkyl group, e.g., methyl; or aryl group, e.g., phenyl, p-chloro-phenyl, or naphthyl; providing a complex of the formula:

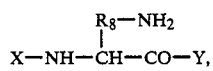
  (8)

where X includes a protecting group, Y includes a solid phase, and R$_3$—NH$_2$ is a side group of Lys, ornithine, or diaminobutyric acid; reacting the carbonyl-containing compound with the complex in the presence of sodium cyanoborohydride to form:

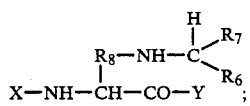
  (9)

cleaving off the solid phase to release the peptide; and purifying the peptide. In preferred embodiments, the carbonyl-containing compound is acetone and the R$_3$—NH$_2$ side group is a side group of Lys.

In the above formulae (2), (5), and (8), Y can include any number of amino acids which have already been bonded sequentially to a solid phase, e.g., a resin, or Y can consist solely of the solid phase. In other words, the non-peptide bond can link any two amino acids of the peptide, and also can link more than one pair of amino acids in the same peptide. Similarly, X in formulae (1) and (8) can include one or two amino acids, although for purposes of ease of automation, it is preferable that X consist only of a protecting group.

The method can be used to provide increased resistance to proteolytic degradation, and thus longer, half-lives in vivo, for any useful synthetic peptides, e.g., human hormones such as LHRH and somatostatin and analogs thereof. The yield, speed, and ease of performance of the method are considerably greater than prior methods using liquid-phase synthesis. In addition, because the method can be used to chemically modify polypeptides in situ, the method provides a simple, fast, and inexpensive means for introducing a variety of alkyl and aryl groups into any useful synthetic polypeptides, e.g., hormones and hormone analogs, e.g., somatostatin and LHRH and their therapeutic analogs.

other features and advantages of the invention will be apparent from the following description of the preferred embodiments thereof, and from the claim.

DESCRIPTION OF THE PREFERRED EMBODIMENTS

Drawings

FIG. 3 is a schematic representation of the synthesis of a chemically modified peptide of the invention featuring an ε-isopropyl group.

Structure

Non-peptide bond

By non-peptide bond is meant a —CH$_2$—NH— moiety between two or more amino acids in a polypeptide chain.

Protecting Group

Any suitable standard amino acid protection group can be used. Examples of such protecting groups are FMOC (Fluorenymethyloxycarbonyl) and butyloxycarbonyl (Boc). These groups prevent non-specific reaction of the amino acids during synthesis of a polypeptide chain.

Solid phase

The solid phase can be any compound to which an amino acid or polypeptide chain may be reversibly chemically coupled, and upon which synthesis of a polypeptide can be performed. Examples of such solid-phases are resins, e.g., chloromethyl resin and benzhydrylamine-polystyrene resin (Vega Biochemical, Inc.).

Amino Aldehyde

Amino aldehydes have the general formula:

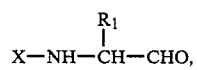

where X and R$_1$ are as described above. These compounds generally are synthesized as described by Fehrentz et al. (1983, Synthesis 676).

Carbonyl-containing Compound

Carbonyl-containing compounds have the general formulae:

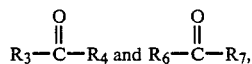

where R$_3$, R$_4$, R$_6$, and R$_7$ are as described above. These compounds are commercially available or can be synthesized using conventional techniques.

Somatostatin Analogs

Somatostatin and its analogs are polypeptides with growth hormone-release-inhibiting activity. Some somatostatin analogs have been described in Coy et al. U.S. Pat. No. 4,485,101, hereby incorporated by reference; and Coy et al. U.S. Ser. No. 775,488, filed Sept. 12, 1985 and now abandoned, assigned to the same assignee as the present application and hereby incorporated by reference.

Synthesis

A. Non-peptide analogs of polypeptides

In general, the synthesis of non-peptide analogs of polypeptides involves the synthesis of a resin-bound protected amino acid or polypeptide chain, and of a protected amino aldehyde, and their reaction in the presence of sodium cyanoborohydride. When the reaction is complete the non-peptide analog can continue to grow, or is cleaved from the resin support and purified by standard procedures.

EXAMPLE 1

Synthesis of D-Phe-Cys-Tyr-D-Trp-CH$_2$-NH-Lys-Val-Cys-Thr-NH$_2$

Figure 1:
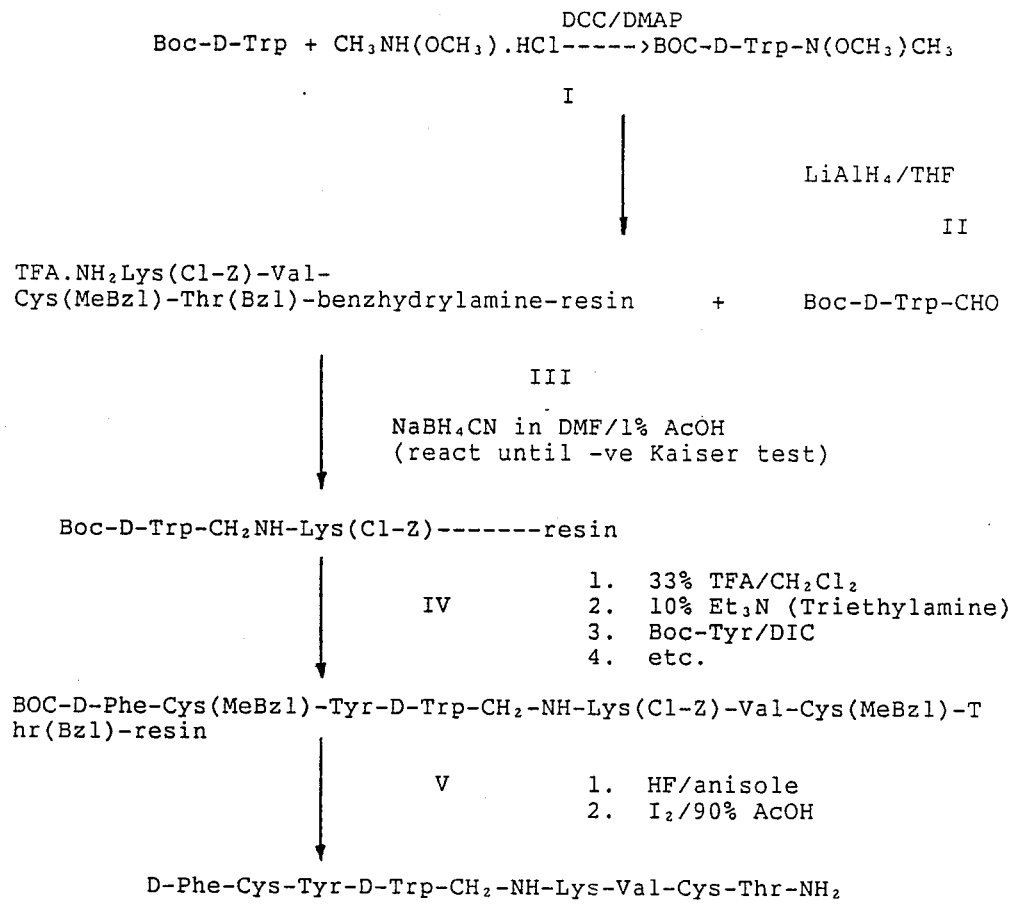
FIG. 1 is a schematic representation of the synthesis of a peptide of the invention featuring a non-peptide bond.

Referring to the FIG. 1, Boc-D-Trp aldehyde (Boc-D-Trp-CHO, 387 mg, 1.25 mmoles) was prepared (Reaction steps I and II) by the method of Fehrentz et al. (id.), and dissolved in 5 ml of dry DMF. Briefly, this involved reacting Boc-D-Trp and CH$_3$NH(OCH$_3$).HCl in the presence of dicyclohexylcarbodiimide (DCC) and 4-dimethyaminopyridine (DMAP) to form an intermediate, which was then reacted with LiAlH$_4$ in tetrahydrofuran (THF) to form the desired aldehyde.

Boc-Lys(Cl-Z)-Val-Cys(MeBzl)-Thr(Bzl)-benzhydrylamine resin (0.5 mmole) was prepared by standard methods using a Beckman 990B automatic peptide synthesizer. The Boc protecting group was removed by treatment with 33% TFA in methylene chloride and the resin TFA salt (TFA NH$_2$Lys(Cl-Z)-Val-Cys(MeBzl)-Thr(Bzl)-benzhydrylamine-resin) was suspended in dry dimethylformamide containing 1% of acetic acid (AcOH).

The above aldehyde and resin TFA salt were mixed, and 100 mg (2 mmoles) of sodium cyanoborohydride added (Reaction III). After stirring for 1 h, the resin mixture was found to be negative to ninhydrin reaction, indicating complete derivatization of the free amino group.

The remaining amino acids of the somatostatin octapeptide (Tyr, Cys, and Phe) were then assembled by standard techniques involving protection steps, carbodiimide couplings and TFA deprotection (Reaction IV).

the free peptide amide was cleaved from the support by treatment with hydrogen-fluoride (HF)/anisole, under standard conditions, and was cyclized by treatment with a slight excess of Iodine (I₂) in 90% acetic acid/water (Reaction V). After evaporation of the solvent, the crude peptide was purified by elution on G-25 in Sephadex TM columns, in 2 M acetic acid, followed by reverse-phase partition chromatography on C₁₈-silica using a linear gradient of 10-30% acetonitrile/0.1% trifluoroacetic acid. The purified peptide (the yield was 63.4 mg) was homogeneous by analytical high pressure liquid chromatography (Hplc) and thin layer chromatograph (Tlc) in several solvent systems. The material gave the expected ratios after amino acid anlysis of an methanesulfonic acid/tryptamine hydrolysate. The presence of the D-Trp-CH₂NH-Lys pseudodipeptide in the correct ratio was demonstrated by comparison with the elution position of an authentic sample of the dipeptide on the amino acid analyser.

EXAMPLE 2

Synthesis of D-Phe-Cys-Tyr-D-Trp-Lys-CH₂NH-Val-Cys-Thr-NH₂

Benzhydrylamine-polystyrene resin (1.30 g, 0.5 mmole) in the chloride ion form was placed in the reaction vessel of a Beckman 990B peptide synthesizer programmed to perform the following reaction cycle: (A) methylene chloride; (b) 33% trifluoroacetic acid in methylene chloride (2 times for 1 and 25 min. each); (c) methylene chloride; (d) ethanol: (e) methylene chloride; (f) 10% triethylamine in chloroform.

The neutralized resin was stirred with Boc-O-benzyl-Thr and diisopropylcarbodiimide (1.5 mmole each) in methylene chloride for 1 h and the resulting amino acid resin is then cycled through steps (a) to (f) in the above wash program. The following amino acids (1.5 mmole) were then coupled successively by the same procedure: Boc-s-methylbenzyl-Cys, Boc-Val. The Boc group was then removed by TFA (trifluoroacetic acid) treatment. Boc-Lys (carbenzoxy)-aldehyde (1.25 mmoles), prepared by the method of Fehrentz et al. (id.), was dissolved in 5 ml of dry DMF (dimethylformamide) and added to the resin TFA salt suspension followed by the addition of 100 mg (2 mmoles) of sodium cyanoborohydride. After stirring for 1 h, the resin mixture was found to be negative to ninhydrin reaction (1 min) indicating complete derivatization of the free amino group.

The remaining amino acids, Boc-D-Trp, Boc-tyr, Boc-S-methylbenzyl-Cys, Boc-D-Phe, of the somatostatin octapeptide were then assembled by standard techniques involving carbodiimide couplings and TFA deprotection. After washing and drying, the completed resin weighed 1.87 g.

The resin was mixed with anisole (4 ml) and anhydrous hydrogen fluoride (36 ml) at 0° C. and stirred for 45 min; to cleave the peptide from the resin support. Excess hydrogen fluoride was evaporated rapidly under a stream of dry nitrogen and the free peptide precipitated and washed with ether. The crude peptide was then cyclized by dissolving it in 800 ml of 90% acetic acid to which is added I₂ in methanol until a permanent brown color was observed. The solution was stirred for 1 h before removing the solvent in vacuo. The resulting oil was dissolved in a minimum volume of 50% acetic acid and eluted on a column (2.5×100 mm) of Sephadex G-25. Fractions containing a major component, as determined by uv (ultraviolet absorption and thin layer chromatography, were then pooled, evaporated to a small volume and applied to a column (2.5×50 cm) of Whatman LRP-1 octadecylsilane (15-20 uM), and eluted with a linear gradient of 10-50% acetonitrile in 0.1% trifluoroacetic acid in water. Fractions were examined by Tlc and analytical Hplc and pooled to give maximum purity. Repeated lyophilization of the solution from water gave 78 mg of the product as a white, fluffy powder.

The product was found to be homogeneous by Hplc and Tlc. Amino acid analysis of an acid hydrolysate confirmed the composition of the octapeptide.

EXAMPLE 3

Synthesis of D-Phe-Cys-CH₂-NH-Tyr-D-Trp-Lys-Val-Cys-Thr-NH₂

This peptide was assembled on benzyhdrylamine resin according to the conditions described in Example 2, using Boc-O-benzyl-Thr, Boc-S-methylbenzyl-Cys, Boc-Val, Boc-Lys, N-benzyloxycarbonyl-Lys, Boc-D-Trp and 2-bromocarbenzoxy-Tyr. Box-Cys(methylbenzyl)-aldehyde was then added to the resin along with NaCNBH₃, as in Example 2. The remaining amino acid, Boc-tert-butyloxycarbonyl-D-Phe, was then added as in Example 2. The final resin weighed 1.84 g.

the resin was subjected to hydrogen fluoride cleavage and I₂ cyclization as described in Example 2. The lyophilized product weighted 89 mg and was found to be homogeneous by Hplc and Tlc. Amino acid analysis of an acid hydrolysate confirmed the composition of the octapeptide.

The above reductive amination method is particularly applicable to peptides containing Trp and Cys residues, and is also compatible with Bzl and Cbz-type side-chain protecting groups.

B. α-N-R analogs of polypeptides

In general, the synthesis of α-N-R analogs of polypeptides, where R is an alkyl or aryl group, involves the synthesis of a resin-bound protected amino acid or polypeptide chain; and of a carbonyl-containing compound, and their reaction in the presence of sodium cyanoborohydride. The net effect of the reaction is to convert the carbonyl group

to a CH group bonded to the nitrogen atom of the α-amino group of the resin-bound amino acid or polypeptide. For example, if the carbonyl compound is formaldehyde

the reaction produces an α-N-methyl moiety. When the sodium cyanoborohydride reaction is complete, the modified peptide can continue to grow, or is cleaved from the resin support and purified by standard procedures.

EXAMPLE 1

Synthesis of The LHRH Agonist pGlu-His-Trp-Ser-TyrD-Ala-N-Me-Leu-Arg-Pro-Gly-NH₂

Figure 2:
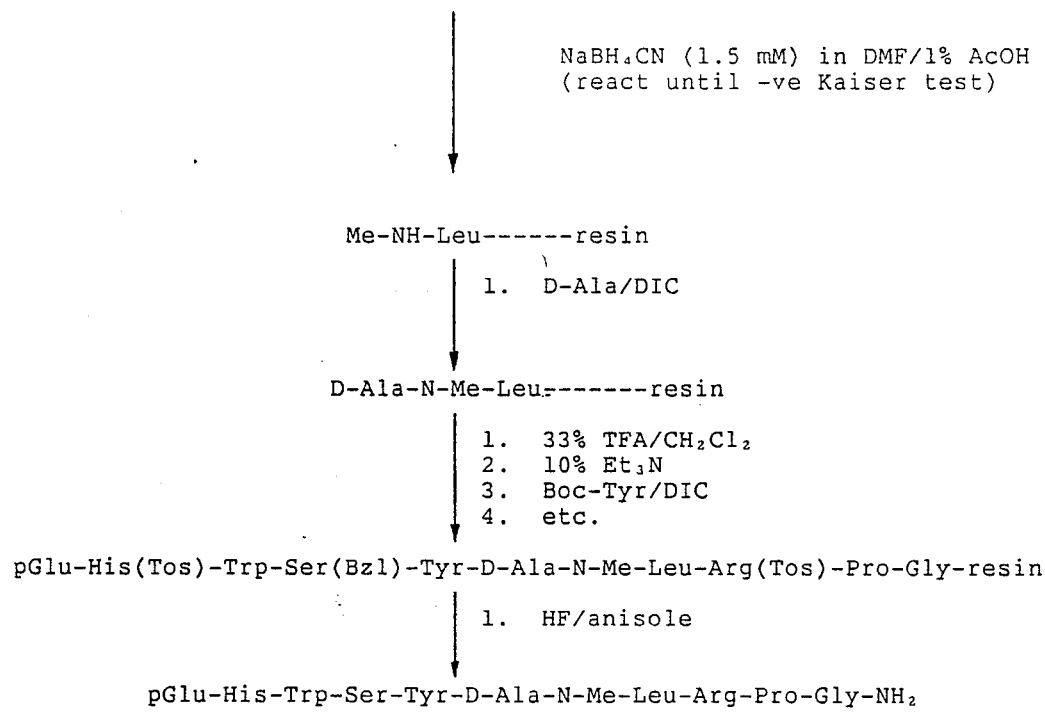
FIG. 2 is a schematic representation of the synthesis of a chemically modified peptide of the invention featuring an α-N-Methyl group.

Referring to FIG. 2, TFA. NH₂-Leu-Arg (Tos)-Pro-Gly-benzhydrylamine resin (0.5 mmole) was prepared by standard methods using a Beckman 990B automatic peptide synthesizer. The resin TFA salt was then mixed with 2 ml formaldehyde (37% formalin), and 1.5 mmoles of sodium cyanoborohydride in DMF (dimethylformamide)/1% ACOH (acetic acid) added. The resin mixture was stirred until it was negative to ninhydrin reaction, indicating complete derivatization of the free amino group to form an N-Methyl amino group.

The remaining amino acids of the polypeptide (D-Ala, Tyr, Ser, Trp, His, and pGlu) were then assembled by standard techniques involving protection steps, carbodiimide couplings, and TFA deprotection.

The free peptide amide was then cleaved from the support by treatment with HF/anisole and purified under standard conditions to yield the desired polypeptide.

C. Side group N-R analogs of polypeptides

In general, the synthesis of side group N-R analogs of polypeptides, where R is an alkyl or aryl group, involves reacting a resin-bound protected amino acid featuring a side chain containing a free amino group, or a resin-bound polypeptide chain containing such an amino acid subunit, with a carbonyl-containing compound in the presence of sodium cyanoborohydride. Amino acids featuring a side chain containing a free amino group include Lys, ornithine, and diaminobutyric acid. The net effect of the reaction is to convert the carbonyl group

into a CH group bonded to the nitrogen of the side chain free amino group of the resin-bound amino acid or polypeptide. For example, if the carbonyl compound is acetone

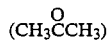

and the amino acid with the free amino-containing side chain is Lys (side chain=—(CH$_2$)$_3$—CH$_2$NH$_2$), the reaction produces an α-N-isopropyl moiety. When the sodium cyanoborohydride reaction is complete, the modified peptide is cleaved from the resin support and purified by standard procedures.

The above-described synthesis can be used to prepare LHRH antagonists, as described below and as described in Coy et al., co-pending U.S. patent application Ser. No. 879,338, filed the same day as this application and now abandoned, assigned to the same assignee as this application, hereby incorporated by reference

EXAMPLE 1

Synthesis of The LHRH Antagonist
Ac-D-Nal-D-Phe-D-Phe-Ser-Tyr-D-Lys(iPr)-Phe-Lys(iPr)-Pro-Ala-NH$_2$ Referring to FIG. 3, Ac-D-Nal-D-Phe-D-Phe-Ser(Bzl)-Tyr (Bzl)-D-Lys(FMOC)-Phe-D-Lys(-FMOC)-Pro-D-Ala-benzhydrylamine (0.25 mmole) resin was prepared by standard methods in a Beckman 990B automatic peptide synthesizer using 33% TFA for removal of the O-BOC protecting groups. The ε-FMOC protecting groups on the Lys residues are completely stable to these acidic conditions, and to subsequent neutralization steps with 10% triethylamine in chloroform. The resin was then treated with 50 ml of a 50% solution of piperidine in DMF (dimethylformamide) for about 12h to remove the FMOC protecting group from the Lys residues.

To react the free ε-amino group of the Lys residues, the resin was mixed with 5ml of acetone, and 1 mmole of sodium cyanoborohydride in DMF/1% acetic acid added. The resin mixture was then stirred until it was negative to ninhydrin reaction (about 3h); the negative ninhydrin reaction indicated that the free ε-amino group had been converted to N-isopropyl amino groups.

The resin was then cleaved from the support by treatment with HF/anisole and purified under standard conditions to yield the desired polypeptide.

Ac-D-Nal-D-Phe-D-Phe-Ser-Tyr-D-Lys(iPr)-Phe-Arg-Pro-D-Ala-amide is prepared in analagous fashion using appropriate modifications of the above-described procedure.

Use

The method of the invention can be used to modify any peptides of therapeutic or veterinary interest, e.g., hormones such as LHRH, TRH, and somatostatin, and analogs thereof. Such modifications can increase the chemical stability and potency of the peptides. In addition, the introduction of N-alkyl or aryl groups will minimize undesirable side effects, e.g., skin irritation, which are often present when the unalkylated or unarylated peptides are administered to human patients. Furthermore, the invention permits the addition of side groups (e.g., isopropyl) to amino acids in an inexpensive way, compared to methods in which the expensive pre-derivatized amino acid itself is employed.

Other embodiments are within the following claims.

We claim:

1. A method of solid-phase synthesis of a polypeptide having a non-peptide bond, comprising the steps of
   (a) providing an amino aldehyde of the formula

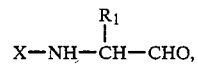

where X comprises a protecting group and R$_1$ is a side group of an amino acid,
   (b) providing a complex of the formula

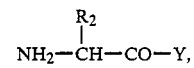

where Y comprises a solid phase and R$_2$ is a side group of an amino acid, and
   (c) reacting said amino aldehyde with said complex in the presence of sodium cyanoborohydride to form

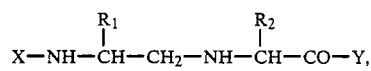

2. The method of claim 1 wherein said amino aldehyde is Trp aldehyde, Lys aldehyde or Cys aldehyde.

3. The method of claim 1 wherein said solid phase is a resin.

4. The method of claim 3 wherein said resin is chloromethyl resin or benzhydrylamine-polystyrene resin.

5. The method of claim 1 further comprising the step of cyclizing said polypeptide.

6. A peptide in which two amino acids are bonded by a non-peptide bond introduced by the method of claim 1.

7. The peptide of claim 6, said peptide being a somatostatin analog.

* * * * *

UNITED STATES PATENT AND TRADEMARK OFFICE
CERTIFICATE OF CORRECTION

PATENT NO. : 4,897,445
DATED : January 30, 1990
INVENTOR(S) : David H. Coy et al.

It is certified that error appears in the above-identified patent and that said Letters Patent is hereby corrected as shown below:

COLUMN 1

As a first sentence and paragraph, insert the paragraph:

--This invention was made in the course of work under a grant or award from the U.S. government; therefore, the U.S. government has rights in the invention.--

Signed and Sealed this

Nineteenth Day of November, 1991

Attest:

HARRY F. MANBECK, JR.

Attesting Officer

Commissioner of Patents and Trademarks